United States Patent [19]

Kawasaki et al.

[11] Patent Number: 5,657,119
[45] Date of Patent: Aug. 12, 1997

[54] SPECTROMETRY USING AN OPTICAL PARAMETRIC OSCILLATOR

[75] Inventors: Shuichi Kawasaki, Tatebayashi, Japan; Randall J. Lane, Brooktondale; Chung L. Tang, Ithaca, both of N.Y.

[73] Assignee: Cornell Research Foundation, Inc., Ithaca, N.Y.

[21] Appl. No.: 382,261

[22] Filed: Feb. 1, 1995

[51] Int. Cl.⁶ .................................. G01J 3/00; G01J 3/10
[52] U.S. Cl. .................................. 356/300; 356/326
[58] Field of Search ................................. 356/300, 326, 356/432; 359/330

[56] References Cited

U.S. PATENT DOCUMENTS

| | | |
|---|---|---|
| 4,213,060 | 7/1980 | Byer et al. . |
| 4,310,762 | 1/1982 | Harris et al. . |
| 4,349,907 | 9/1982 | Campillo et al. . |
| 4,544,274 | 10/1985 | Cremers et al. . |
| 5,017,806 | 5/1991 | Edelstein et al. . |
| 5,117,126 | 5/1992 | Geiger . |
| 5,134,622 | 7/1992 | Deacon . |
| 5,257,085 | 10/1993 | Ulich et al. .............................. 356/328 |
| 5,259,917 | 11/1993 | Ohmer et al. . |
| 5,291,503 | 3/1994 | Geiger et al. . |

OTHER PUBLICATIONS

Kawasaki et al, "Thermal Lens Spectrophotometry Using a Tunable Infrared Laser Generated by a Stimulated Raman Effect", Analytical Chemistry, vol. 59, No. 3, Feb. 1, 1987, pp. 523–525.

*Primary Examiner*—F. L. Evans
*Attorney, Agent, or Firm*—Jones, Tullar & Cooper, P.C.

[57] ABSTRACT

A thermal lens spectrometer utilizes a continuously tunable optical parametric oscillator (OPO) to provide practical, easy-to-build, reliable spectrometer for measuring a wide variety of sample materials over a wide spectral range. A flow cell is placed in the path of the output beam from a tunable optical parametric oscillator, and material to be analyzed is placed in the cell. A laser probe beam is also directed into the cell coaxially with the OPO output beam. The OPO output beam acts as a pump, and the output probe beam from the cell is directed to an intensity sensor. The OPO is tuned over a selected frequency range, under computer control, for example, to produce an output probe beam having an intensity representing the spectral response of the material to be analyzed.

19 Claims, 3 Drawing Sheets

SPECTROMETRY USING AN OPTICAL PARAMETRIC OSCILLATOR

This invention was made with Government support under Contract No. F49620-93-3-0016 awarded by the U.S. Department of the Air Force, and under Grant No. ECS 9108570 of the National Science Foundation. The Government has certain rights in the invention.

BACKGROUND OF THE INVENTION

The present invention relates, in general, to tunable laser spectroscopy, and more particularly to laser spectroscopy utilizing an optical parametric oscillator as a continuously tunable laser source.

For many spectroscopic and spectrometric applications, such as nonlinear, photothermal, and fluorescence spectrometry, widely and continuously tunable laser sources are required. Until recently, dye lasers have been generally used for tunable laser spectroscopy. However, the tuning range of dye lasers tends to be severely limited. Each dye can cover only a few hundred angstroms, and the total range that can be covered by laser dyes is limited from approximately 400 nm to 1 µm. To extend beyond the primary dye laser tuning range, complicated nonlinear optical techniques are required.

Thermal lens spectrometry is known as a highly sensitive method for detecting very small quantities of material by absorption of visible, ultraviolet or infrared light from a laser source. This method takes advantage of the thermal lens effect, which is a thermally induced alteration of the index of refraction of an absorbing medium which occurs when a laser beam is passed through the medium. In the thermal lens device described in U.S. Pat. No. 4,310,762, a converging beam derived from a coherent, collimated beam is passed through a reference cell. The converging beam is slightly modified by the change in index within the cell, due to the thermal lens effect. The modified beam then is passed through a sample cell containing the identical medium, with an additional medium which is to be identified. The reference cell and the sample cell are located at points in the beam path so that any modification in the beam caused by a change in the index of refraction in the reference cell is canceled by the same medium in the sample cell. Any detectable modification in the beam, e.g. expansion or divergence, as it evolves from the sample cell is due to the thermal lens effect caused by an additional pump beam directed onto the material to be identified.

U.S. Pat. No. 4,544,274 also uses the thermal lens phenomenon for measuring weak optical absorptions when a cell containing sample is inserted into a normally continuous-wave laser-pumped dye laser cavity. The pulsewidth of the resulting pulsed laser output is related to the sample absorbtivity by a simple calibration curve.

SUMMARY OF THE INVENTION

Since the invention of the laser, there has been a great deal of interest in truly continuously tunable laser sources that cover a wide spectral range. Recent developments in the use of nonlinear optical crystals in optical parametric oscillators have made it possible to develop spectroscopic and spectrometric systems for a wide variety of applications. It has now been found that optical parametric oscillator (OPO) devices are particularly valuable in thermal lens spectroscopy for use in a wide range of environmental and analytical chemistry applications.

Briefly, in accordance with the present invention a thermal lens spectrometer utilizes a spectrometry flow cell placed in the path of a tunable pump beam such as the signal beam from a solid state, tunable OPO utilizing one or more nonlinear crystals. The sample material to be analyzed is placed in the cell, and the OPO pump beam is directed through the cell. The pump beam is then eliminated by a prism and a bandpass filter following the cell. A probe laser beam, from an He-Ne laser, for example, is also directed through the cell coaxially with the OPO beam. This probe beam is directed through a pin-hole onto a sensor such as a photomultiplier, which measures the intensity of the probe light leaving the cell as the OPO is tuned through its output tuning range, or a selected portion thereof, to obtain the spectrum of the material being analyzed as a function of OPO beam wavelength. The change in the intensity of the probe beam is due to the wavelength-dependent heating of the sample in the flow cell due to the absorption of the pump beam, which is the OPO signal beam.

The solid state spectroscopic system of the invention is compact, and has high output power and efficiency as compared to the conventional sources, without the need for an amplifier stage, making possible highly sensitive measurements, particularly in thermal lens spectrometry (TLS). The high sensitivity available in such TLS permits measurements with excellent spacial resolution while using only a small sample volume. Further, the characteristics of the present device make it suitable for remote sensing.

BRIEF DESCRIPTION OF THE DRAWINGS

The foregoing, and additional objects, features and advantages of the present invention will become apparent to those of skill in the art from the following detailed description of a preferred embodiment, taken with the accompanying drawings in which.

DETAILED DESCRIPTION OF THE PREFERRED EMBODIMENT

Figure 1:
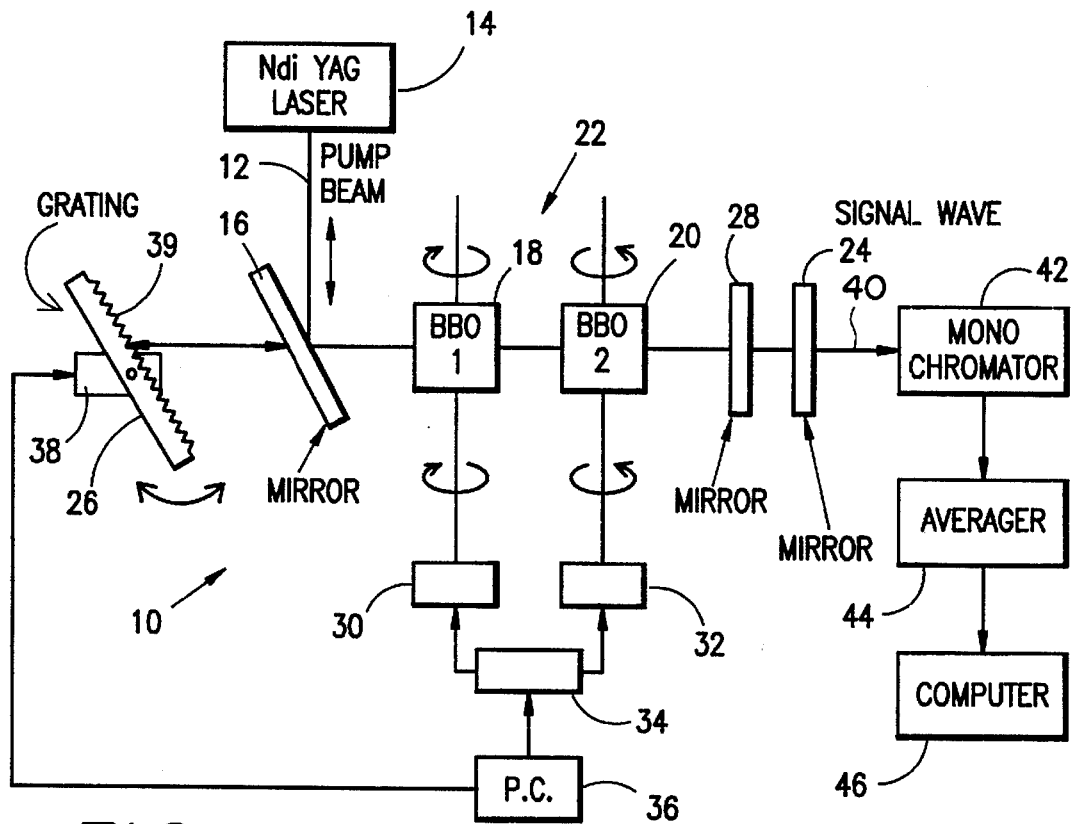
FIG. 1 is a diagrammatic illustration of a typical optical parametric oscillator suitable for use in spectrometry.

FIG. 1 illustrates the cavity configuration of a typical tunable optical parametric oscillator (OPO) 10 suitable for use in the present invention. An example of such an oscillator is described more fully in an article "High-efficiency and Narrow-linearwidth Operation of a Two-crystal β-$BaB_2O_4$ Optical Parametric Oscillator", W. R. Bosenberg et al., Appl. Phys. Lett. 55, 1952–1954 (1989). The basic principle of the OPO is simple. UV photons (at 355 nm, for example) from a pump beam 12 produced as the third harmonic of a Nd:YAG pumping laser 14 are directed by mirror 16 through two nonlinear Beta Barium Borate (β-$BaB_2O_4$, or BBO) crystals 18 and 20, where they break down by spontaneous and stimulated emission into lower-frequency photons called the signal (visible) and the idler (infrared) photons. The crystals 18 and 20 are included in a Fabry-Perot cavity 22 formed by an output mirror 24 and a grating 26, the cavity providing the optical feedback which leads to oscillation of the OPO. Mirror 28 in cavity 22 and mirror 16 transmit the signal and idler, but reflect the UV pump photons.

The grating is oriented in the Littrow configuration so as to reduce the oscillator linewidth to 0.2–0.6 nm throughout the tuning range of the oscillator. Two BBO crystals are used to compensate for the walk-off effect because the Poynting vector and the k-vector of the pump wave are not in the same direction. The crystals may be grown by using the known top-seeded high-temperature solution growth technique. The lengths of the crystals are 9 and 8.5 mm and they are cut for type-I phase matching at 28.6°.

The two crystals are mounted on separate rotational stages 30 and 32, respectively, that are connected to a motor controller 34, which is in turn controlled by a standard personal computer 36. This system allows the two crystals to be set simultaneously to a phase-matching angle corresponding to the desired output wavelength. The grating 26 (Milton Roy) has 1800 grooves/mm with a blaze angle of 26.5°. The grating is also placed on the same kind of rotational stage 38 and is controlled by the computer to set the desired angle. The grooves 40 on the grating are positioned normal to the polarization of the OPO signal beam to improve the broadband diffraction efficiency and the line-narrowing effect.

The pump source 14 for the OPO is a Q-switched Neodymium-doped Yttrium Aluminum Garnet (Nd:YAG) laser system followed by third-harmonic generation (THG). The pump beam diameter is reduced to 2 mm by use of a telescope; a typical pulse property may be 12 mJ with a 5–6 ns pulse duration at 355 nm. The pump beam is steered through the OPO cavity by use of mirror 16 and reflected back along the same optical axis by use of mirror 28. Both mirrors are 355 nm high reflectors. The incident angles are 55° and 0°, respectively, for mirrors 16 and 28. The output coupler of the OPO 10 is a standard multilayer dielectric-coated mirror 24 with 50% reflectivity at 550 nm, which allows signal wave 40 to exit the cavity. The resonated OPO signal wave is diffracted by the grating, and the first-order diffracted beam is reflected back along the cavity axis. This Littrow configuration minimizes loss from the grating. The cavity length is 75 mm from the center of the grating to the surface of mirror 24.

The linewidth of the OPO signal wave 40 may be measured by using a 0.5 m monochromator 42 equipped with a photodiode. In a test of the equipment, wavelength resolution was set to 0.2 nm, which also corresponded to the monochromator's wavelength accuracy. The signal from the photodiode in monochromator 42 was sent to a boxcar averager 44 (EG&G Model 162) and then read into a computer 46. The spectrum was displayed in real time on the computer screen. The intensity fluctuation of the OPO output was also measured. A hot mirror was used to isolate the signal wave from the idler.

Figure 2:
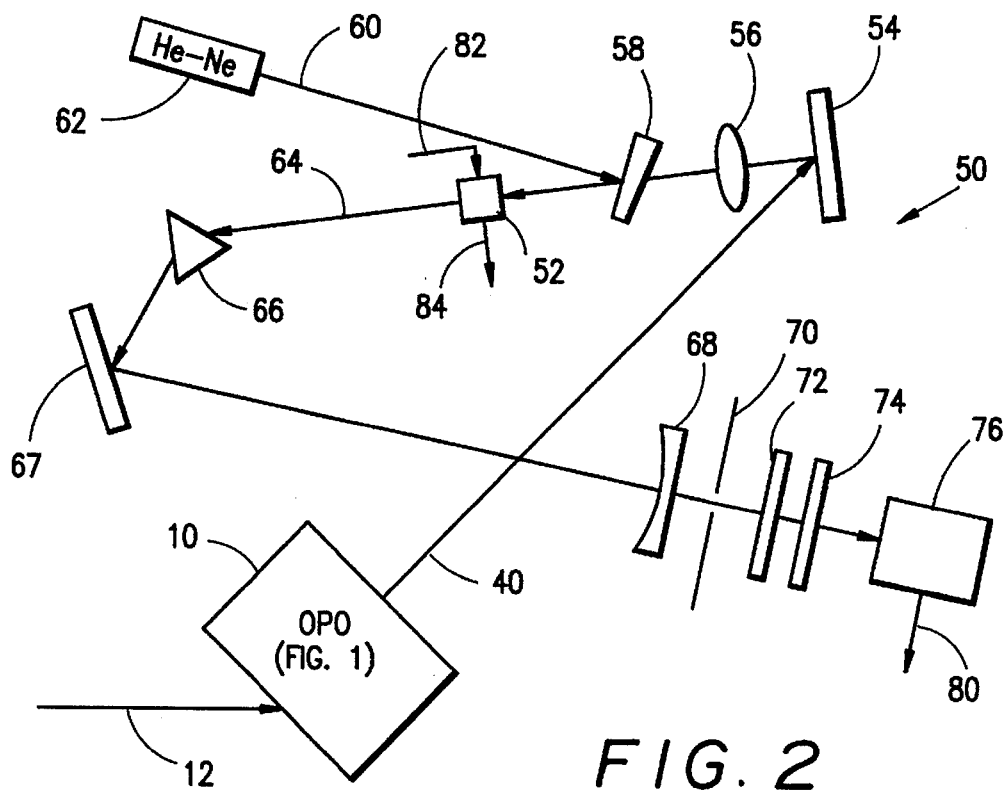
FIG. 2 is a diagrammatic illustration of a thermal lens spectrometer using the optical parametric oscillator of FIG. 1.

FIG. 2 is a block diagram of a thermal lens spectrometer 50 based on a direct incidence system of the type described by K. Mori et al., "Determination of Nitrogen Dioxide by Pulsed Thermal Lens Spectrophotometry" Anal. Chem. 55, 1075–1079 (1983) and by S. Kawasaki et al. "Thermal Lens Spectrophotometry Using a Tunable Infrared Laser Generated by a Stimulated Raman Effect", Anal. Chem. 59, 523–525 (1987). In this spectrometer, the OPO output signal wave 40 from the OPO 10 is used as a pump beam, and is focused into a 1 cm sample flow cell 52 (Hellma Cells, Inc.) by way of a mirror 54, a lens 56, and a quartz wedge 58. A beam 60 from an He-Ne laser 62 (Spectra-Physics, Inc. Model 105-1) is directed to the surface of wedge 58 and is reflected coaxially with the OPO pump beam 40 into the cell 52. The beam 60 is used as the probe beam and passes through the cell without focusing, producing a sample output probe beam 64 which is directed through a quartz prism 66 to a mirror 67. The mirror 67 directs the sample output probe beam 64 through a lens 68 which expands it to a 10 mm diameter, through a pinhole aperture 70, through a polarizer 72 and through a bandpass filter 74 to a photomultiplier 76 (Thorn EMI Electron Tubes, Ltd., 9658R). The pinhole may have an aperture of 1.2 mm, with the bandpass filter being centered at the wavelength of the He-Ne probe; i.e., at 632.8 nm, and with the photomultiplier measuring the intensity of the beam center. The intensity spectrum may be supplied by way of line 80 to a personal computer for display on the computer screen in real time. In a test of the equipment, a sample of nitrogen dioxide (supplied by Matheson) was diluted to 0.5% in dry air and delivered to the flow cell 52 by way of line 82. The flow rate of the sample was 40–50 cc/min and the outlet gas line 84 was then bubbled through an NaOH solution (not shown) and discharged.

To maintain narrow linewidth oscillation over wide range, it is important to have synchronized operation and precise alignment between the two crystals 18 and 20 and the grating 26. The generated wavelength that depends on the crystal angle for two crystals over the entire tuning range was measured in the above-noted experimental set-up, and an equation was derived for the tuning curve with a fifth-order polynomial fit to these data. The error in selecting a given wavelength was confirmed to be within the accuracy of the rotational stage.

Figure 3:
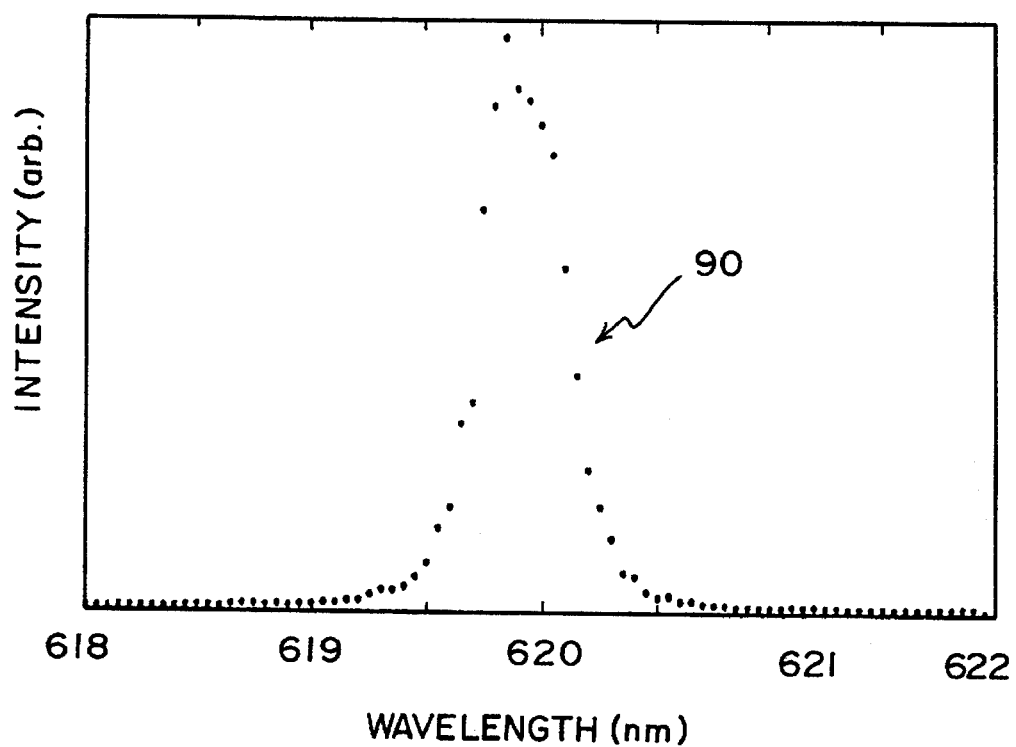
FIG. 3 is a graphical illustration of the intensity vs wavelength spectrum of a typical OPO.

FIG. 3 shows a typical OPO output at 620 nm. The spectrum indicated by curve 90 was obtained by using the first-order diffracted beam from the Littrow configured grating, which was blazed for optimum efficiency around this range. The output beam 40 was measured in 0.05 nm steps and 30 points were averaged at each step. The full width at half-maximum (FWHM) linewidth is estimated to be 0.45 nm from the spectrum. The observed value without a grating is close to 1.5-nm FWHM. Thus, one can successfully use the grating to reduce the linewidth by a factor of 3 at this wavelength. The spectral shape of curve 90, which is almost symmetric, also indicates that the angles of two crystals are well synchronized with that of the grating.

Above 620 nm the linewidth increased slightly to 0.5–0.6 nm, which is cause by broadening of the phase-matching bandwidth of the crystal near the degenerated point. Careful alignment of the crystal angle and grating produces narrower oscillation. Precise alignment of the cavity cannot be maintained during automatic scanning since the accuracy of the rotational stage is limited to 0.0050°. This, however, can be improved with a higher resolution grating. A 2400-grooves/mm grating gives a linewidth of 0.15 nm at 650 nm without sacrificing efficiency significantly. One can achieve a narrower linewidth by inserting an étalon over the wide spectral range. The Littman configuration can also decrease the linewidth to that of the étalon configuration, but its low efficiency still remains a problem. The linewidth of the OPO is also affected by the linewidth and divergence of the pump beam. However, one can solve these problems by using an injection-seeded Nd:YAG laser. A single longitudinal mode can be obtained with that pump laser, but the difficulty in stabilizing the cavity leads to a limited tuning range. Finally, a proper configuration is chosen depending on the application, trading off the advantages of simplicity, wide tunability, high efficiency, and narrow linewidth.

Figure 4:
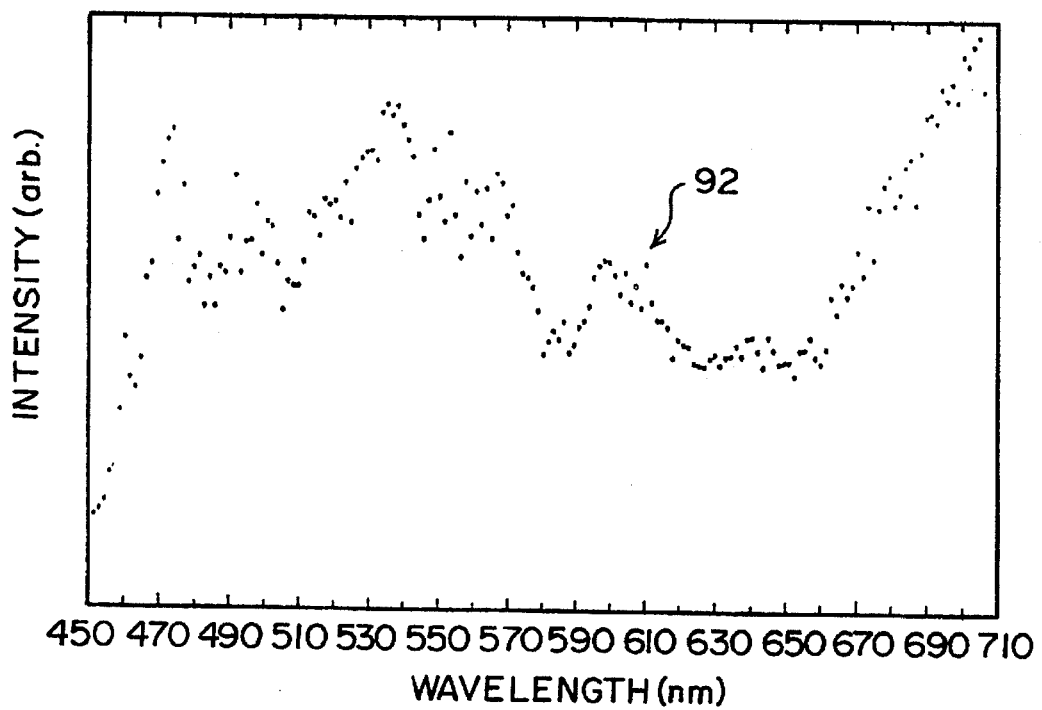
FIG. 4 is a graphical illustration of the tuning curve of the signal wave of an OPO.

Curve 92 in FIG. 4 shows the output intensity of the signal wave of the OPO as a function of wavelength from 450 to 706.5 nm. The OPO was scanned at 1.5 nm/step and 50 points were averaged at each step. The intensity was corrected for the spectral response of the photodiode that was used for the measurements. The scanning time was approximately 14 min. This spectrum 92 shows the intensity of the signal wave. Since the hot mirror used cannot isolate the signal wave from its corresponding idler at wavelengths over 680 nm, the intensity above this region includes that of the idler wave. A jump in the output intensity around 475 nm is seen from étalon effects that are due to internal reflections that are no longer lost from the cavity when the surfaces of each crystal rotate into a position that is normal to the cavity axis. The conversion efficiency was greater than 10% for most of the tuning range and 13% at 650 nm. It was 12% when a 2400-groove/mm grating was used, and 3% with an additional étalon at 650 nm. This spectrum was measured to show that there are no spectral gaps over the entire tuning range. Therefore, the spectral transmission variation of the hot mirror was not considered, which is the main cause of irregular intensity fluctuation. The wavelength dependence of the intensity also depends on the transmittance of the output coupler 24.

The tunable range of this system is actually 450–1675 nm, limited by the cavity mirrors that were used. The wavelength accuracy of this system was measured for several wavelengths over the tuning range and was confirmed to be within half of the linewidth of the oscillation beam at each point. The response of the system depends mostly on the rotational rate and the minimum step of the rotational stage. The crystals and grating were directly mounted on the rotational stages in the experimental set-up; therefore, any wavelength could be selected within a few seconds, although the scanning time was limited by the repetition of the Nd:YAG laser (10 Hz) and the desired amount of averaging at each point.

This compact, solid-state BBO OPO system has several desirable performance characteristics for spectroscopic applications. High output power and efficiency relative to conventional sources without an amplifier stage make sensitive measurements possible, especially for spectrometry such as thermal lens spectrum (TLS), which is known as a highly sensitive analytical method. For example, it has been reported that TLS is almost 1000 times more sensitive than conventional absorption spectrometry for probing $NO_2$ diluted in air. Because of this sensitivity, only a small sample volume is needed and excellent spatial resolution can be obtained. Accordingly, the actual sample volume needed for the thermal lens signal is defined only by the beam cross section and the confocal distance of the focusing lens. In the experimental set-up described above, the OPO beam was tightly focused by lens 56 which led to a short confocal distance (<1 mm) which allowed the use of a 1-cm flow cell. The thermal lens signal was strong enough to obtain a spectrum comparable with that measured with a 1.2–1.3% sample with a 7.5 cm cell. Furthermore, the BBO OPO TLS system makes a fingerprinting assignment (which has been of interest but unachievable with conventional dye lasers) feasible because of its broad tunability. These characteristics are quite suitable for remote-sensing device.

Figure 5:
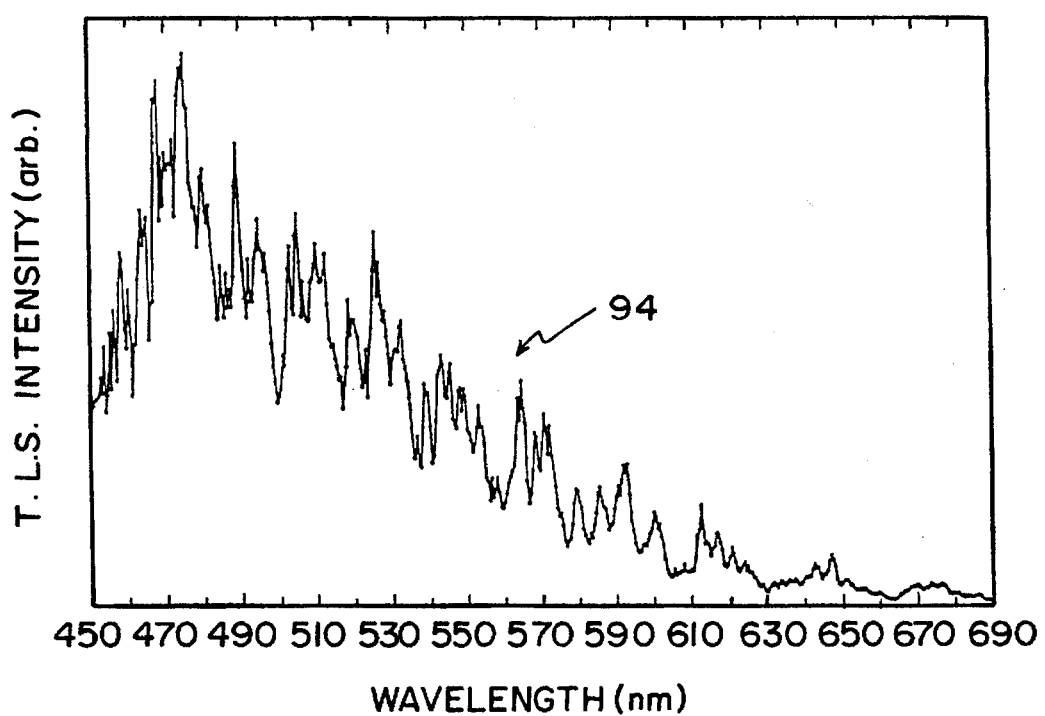
FIG. 5 is the thermal lens spectrum of $NO_2$ from 450 to 690 nm, utilizing the apparatus of FIG. 2.

FIG. 5 shows a thermal lens spectrum 94 of $NO_2$ from 450 to 590 nm. Each peak corresponds well with previously reported spectra. In this experiment the idler was not isolated. However, absorption of the idler wavelength by the sample was small and so could be neglected. Since the intensity of the thermal lens input signal 40 is proportional to the OPO power, intensity variations over the tuning range will affect the amplitude of the spectral peaks. This is the reason the peaks under 470 nm are relatively small. During a scan over such a wide spectral range, dispersion of the focusing lens and the beam splitter influences the signal intensity. In this experiment, however, the confocal distance was estimated to be less than 1 mm. Over the spectral range, the focal point and the focal length changed by less than 0.1 mm and a few millimeters, respectively. Since the direct incidence method was employed, these factors had no significant effect on the spectrum.

Figure 6:
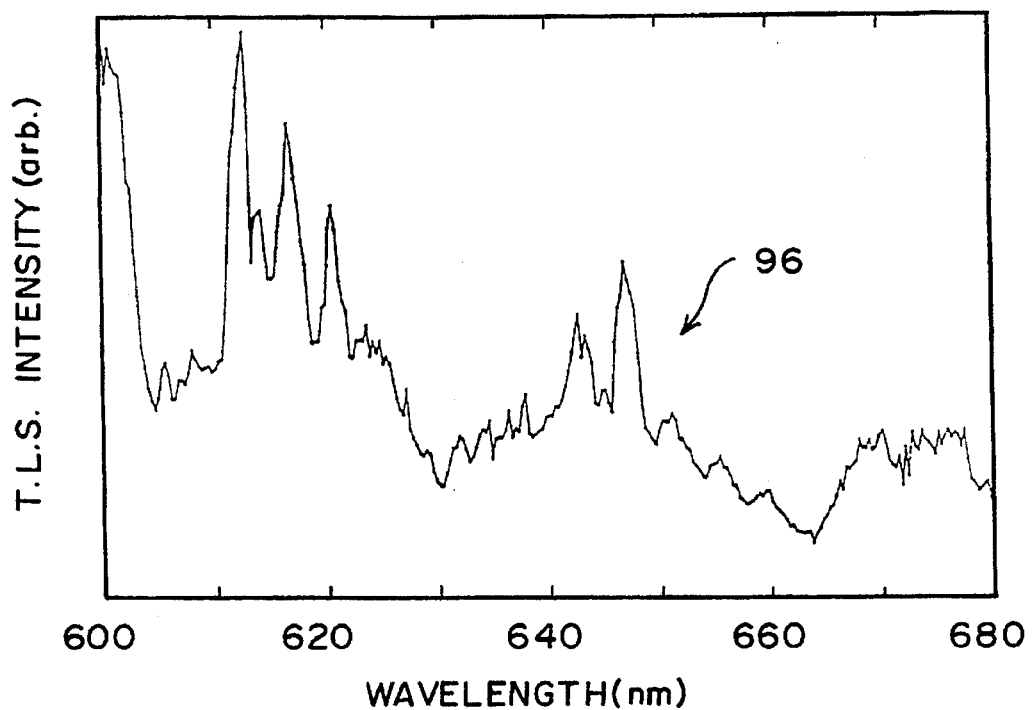
FIG. 6 is the thermal lens spectrum of $NO_2$ from 600 to 680 nm.

FIG. 6 shows the spectrum 96 of the same sample between 600 and 680 nm, reproducing exactly the known spectrum of this molecule. Because $NO_2$ shows a complicated spectrum, finer details of the spectrum cannot be resolved at this resolution. As the excitation beam is tuned toward the wavelength of the He-Ne laser, it can spuriously give a positive signal at the photomultiplier tube. However, since the OPO beam is polarized linearly and has a fast rise time, it can easily be separated by using a polarizer and by changing the gate position of the boxcar.

Thus, there has been disclosed a computerized BBO OPO system with a narrow linewidth oscillation of 0.2–0.6 nm over its visible tuning range. The performance of this system is demonstrated by measuring the thermal lens spectrum of $NO_2$, which illustrates that the tunability of the system, 450–1675 nm, is much broader than that of commercially available dye laser systems that require dye changes to achieve a wide spectral region. The present system also tunes more quickly and easily over its whole tuning range. The OPO system is completely solid state (except for the YAG laser pumped by a water-cooled flash lamp) and consists of commercially available components, making it a very practical tunable laser system. The system succeeded in measuring the entire visible thermal lens spectrum of $NO_2$ in a single scan with adequate resolution to resolve the important peaks, thus demonstrating excellent pointing stability and wide tunability.

Although the invention has been described in terms of a particular OPO, as pump source, with a particular laser as the probe, it should be understood that the system of the invention is not linked to these particular devices. Nor is the system limited to the particular sample or wavelength described herein, but is limited only by the scope of the following claims.

What is claimed is:

1. A system for tunable laser spectroscopy, comprising:
   a light-transmitting cell containing a sample material;
   a tunable optical parametric oscillator pump source having an output selectable wavelength pump output beam to be directed through said cell;
   a laser probe beam;
   an optical path directing said laser probe beam through said cell substantially coaxially with said pump output beam, said probe beam passing through said cell to produce a cell output beam having an intensity which varies with the selected wavelength of said optical parametric oscillator pump source output beam in accordance with said sample material.

2. The system of claim 1, further including an optical sensor for detecting the intensity of said cell output beam to produce an intensity spectrum of said sample material.

3. The system of claim 2, wherein said optical parametric oscillator is variable over a wide spectral range.

4. The system of claim 3, further including a common optical path for said pump beam and said probe beam to direct said beams coaxially to said cell.

5. The system of claim 4, further including a mirror directing said pump beam from said pump source to said common optical path.

6. The system of claim 5, further including a sample inlet and a sample outlet for said cell for passing said sample through said cell.

7. The system of claim 5, wherein said optical parametric oscillator includes a rotatable tuning crystal.

8. The system of claim 7, wherein said crystal is mounted for rotation on a motor-driven support, said system further including a motor controller for regulating the rotation of said support to controllably tune said oscillator.

9. The system of claim 1, wherein said optical path directing said laser probe beam to said cell includes a reflective surface.

10. The system of claim 1, wherein said optical path further includes an optical reflector for directing said pump beam through said cell.

11. The system of claim 10, further including a lens directing said pump beam through said cell.

12. The system of claim 1, further including a detector for receiving said cell output beam.

13. The system of claim 12, wherein said detector includes a photosensor, a prism, and a bandpass filter for passing said cell output beam to said photosensor and for rejecting the pump output beam.

14. The system of claim 13, further including a reflector directing said cell output beam to said detector.

15. The system of claim 1, further including a laser source for said probe beam, said optical path including a reflector directing said probe beam from said laser source through said sample cell.

16. The system of claim 15, wherein said optical path further includes means directing said pump output beam through said reflector and through said sample path, said probe beam and said pump beam being substantially coaxial from said reflector through said cell.

17. The system of claim 16, further including an optical sensor responsive to said cell output beam and an optical filter between said cell and said sensor for preventing said pump output beam from reaching said sensor.

18. The system of claim 17, further including a controller for tuning said optical parametric oscillator to thereby controllably vary the wavelength of said pump output beam and to vary the intensity of said cell output beams as a function of the wavelength of said pump output beam.

19. The system of claim 18, wherein said optical parametric oscillator is variable over a wavelength range of about 450–1675 nm.

* * * * *